(12) United States Patent
McCully

(10) Patent No.: US 9,682,131 B2
(45) Date of Patent: *Jun. 20, 2017

(54) COMPOSITIONS AND METHOD FOR UTILIZATION OF THIORETINAMIDE IN THERAPY OF DEGENERATIVE DISEASES OF AGING

(71) Applicant: Kilmer S. McCully, Winchester, MA (US)

(72) Inventor: Kilmer S. McCully, Winchester, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/757,363

(22) Filed: Dec. 22, 2015

(65) Prior Publication Data
US 2016/0199465 A1 Jul. 14, 2016

Related U.S. Application Data

(63) Continuation of application No. 13/067,504, filed on Jun. 6, 2011, now Pat. No. 9,216,209.

(51) Int. Cl.
| | |
|---|---|
| *A61K 31/381* | (2006.01) |
| *A61K 38/48* | (2006.01) |
| *A61K 38/54* | (2006.01) |
| *A61K 8/67* | (2006.01) |
| *A61K 31/16* | (2006.01) |
| *A61K 38/46* | (2006.01) |
| *A61K 38/47* | (2006.01) |
| *A61K 31/07* | (2006.01) |
| *A61K 45/06* | (2006.01) |
| *A61K 35/39* | (2015.01) |
| *A61K 31/00* | (2006.01) |

(52) U.S. Cl.
CPC .......... *A61K 38/4826* (2013.01); *A61K 8/671* (2013.01); *A61K 31/00* (2013.01); *A61K 31/07* (2013.01); *A61K 31/16* (2013.01); *A61K 35/39* (2013.01); *A61K 38/465* (2013.01); *A61K 38/47* (2013.01); *A61K 38/54* (2013.01); *A61K 45/06* (2013.01); *C12Y 301/01003* (2013.01); *C12Y 302/01001* (2013.01); *C12Y 302/01002* (2013.01); *C12Y 304/21004* (2013.01)

(58) Field of Classification Search
CPC .............................. A61K 31/381; A61K 38/48
See application file for complete search history.

(56) References Cited

U.S. PATENT DOCUMENTS

| | | | |
|---|---|---|---|
| 4,255,443 A | 3/1981 | McCully | |
| 4,383,994 A | 5/1983 | McCully | |
| 4,618,685 A | 10/1986 | McCully | |
| 4,925,931 A | 5/1990 | McCully | |
| 5,565,558 A | 10/1996 | McCully | |
| 5,817,621 A * | 10/1998 | Goudzenko | A61K 8/35 424/94.2 |
| 6,054,595 A | 4/2000 | Kazimir | |
| 6,287,818 B1 | 9/2001 | Kazimir et al. | |
| 6,437,003 B1 | 8/2002 | Roullet et al. | |
| 6,686,172 B2 | 2/2004 | Matsuyama et al. | |
| 6,696,082 B2 | 2/2004 | McCully | |
| 6,867,014 B2 | 3/2005 | Kawasaki et al. | |
| 6,919,072 B2 | 7/2005 | Varani et al. | |
| 7,030,265 B2 | 4/2006 | Sin et al. | |
| 7,135,306 B2 | 11/2006 | Esaki et al. | |
| 2005/0147665 A1 | 7/2005 | Horrobin et al. | |
| 2010/0113352 A1 | 5/2010 | Millstein | |

OTHER PUBLICATIONS

McCully Kilmer S.; American Journal of Pathology 1969; 56:111-128.
Kanwar Y.S., et al.; Pediatric Research 1976; 10:598-609.
McCully Kilmer S.; Cancer Research 1976; 36:3198-3202.
Jacubowski H.; FEBS Letters 1993; 317:237-240.
McCully Kilmer S., et al.; Chemotherapy 1977; 23:44-49.
McCully Kilmer S., et al.; Proceedings of the Society for Experimental Biology and Medicine 1985; 180:57-61.
McCully Kilmer S., et al.; Carcinogenesis 1987; 8:1559-1562.
McCully Kilmer S., et al.; Proceedings of the Society for Experimental Biology and Medicine 1989; 191:346-351.
Kazimir M., et al.; Research Communications in Molecular Pathology and Pharmacology 2002; 5, 6:179-198.
McCully Kilmer S.; Nature 1971; 231:391-392.
Clopath P., et al.; Science 1976; 192:372-374.
McCully Kilmer S.; Annals of Clinical and Laboratory Science 1975; 5:147-152.
McCully Kilmer S.; American Journal of Pathology 1972; 66:83-95.
McCully Kilmer S.; Annals of Clinical and Laboratory Science 1994; 24:27-59.
Ingenbleek Y., et al.; Nutrition 2002; 18:40-46.
Carballal S., et al.; Biochemistry 2008; 47:3194-3202.
Samuel W., et al.; Journal of Cellular Physiology 2006; 209:854-865.
Hail N Jr. et al.; Apoptosis 2006; 11:1677-1694.
Miles EW et al.; Journal of Biological Chemistry 2004; 279:29871-29874.
Kim J et al.; Oncology Reports 2009; 21:1449-1454.
John Beard; The Enzymatic Treatment of Cancer and its Scientific Basis; originally published in 1911, and republ. by New Spring Press, NY, 2010 with a foreword by N. Gonzalez.
Acevedo HF et al.; Cancer 1995; 76:1467-1475.
Nicholas Gonzalez and Linda Isaacs; The Trophoblast and the Origins of Cancer published by New Spring Press, New York, 2009.

(Continued)

*Primary Examiner* — Rosanne Kosson
(74) *Attorney, Agent, or Firm* — Breneman & Georges

(57) ABSTRACT

A process for the endogenic catabolism of homocysteine and the control of homocysteine levels for treating disease and the degenerative diseases of aging is provided along with pharmaceutical compositions having thioretinamide, retinol or combinations thereof in combination with an enzyme or a pro-enzyme. The process includes the catabolism of homocysteine thiolactone in cells and tissues by catalyzing the reaction of homocysteine thiolactone with an enzyme-bound retinoic acid to increase the bioavailability of thioretinamide in diseased and aged cells and tissue.

26 Claims, No Drawings

(56) References Cited

OTHER PUBLICATIONS

Perla-Kajan J et al.; Amino Acids 2007;32:561-572.
Gaull G et al.; Pediatric Research 1972; 6:538-547.
Otto Warburg; Warburg O Science 1956; 123:309-314.
Schneider et al.; Cancer Research 1943; 3:353-357.
The Nitrilosides in the Prevention and Control of Cancer; the McNaughton Foundation, 1962.
Sen U et al.; American Journal of Physiology Renal Physiology 2009; 297:F410-F419.
Olson KR; Antioxidants and Redox Signaling 2010; 12:1219-1234.
Chang L et al; Amino Acids 2008; 34:573-585.
Longevity, Senescence, and the Genome by Finch CE, University of Chicago Press, Chicago: 1990, (Title pages of book and pp. 380-385 and pp. 398-400).
Naruszewicz et al.; Nutrition, Metabolism, and Cardiovascular Disease 1994; 4:70-77.
Ravnskov et al.; Annals of Clinical and Laboratory Science 2009; 39:3-16.
Fife B; Stop Alzheimer's Now, Picadilly Books, Colorado Springs CO, 2011, pp. 115-138.
Smith TJ, et al.; Biochimica Biophysica Acta 1991; 1075:119-122 Abstract only.
McCully Kilmer S.; Annals of Clinical and Laboratory Science 1994; 24:134-152.
Johannsson H., et al.; Cancer Research 2008; 68:(22) 9512-9518.
McCully Kilmer S. et al.; Atherosclerosis 1990; 83(3):197-205.
Farmer, Current Atherosclerosis Reports 2009; 11:87-92.

* cited by examiner

COMPOSITIONS AND METHOD FOR UTILIZATION OF THIORETINAMIDE IN THERAPY OF DEGENERATIVE DISEASES OF AGING

CROSS REFERENCE TO RELATED APPLICATIONS

This application is a continuation application of U.S. application Ser. No. 13/067,504 now U.S. Pat. No. 9,216,209.

STATEMENT REGARDING FEDERALLY SPONSORED RESEARCH OR DEVELOPMENT

Not applicable.

INCORPORATION BY REFERENCE OF MATERIAL SUBMITTED ON COMPACT DISC

Not applicable.

REFERENCE TO A "MICROFICHE APPENDIX"

Not applicable.

BACKGROUND OF THE INVENTION

1. Field of the Invention

A method and compositions are for metabolic control of thioretinamide utilization in prevention and treatment of cancer, arteriosclerosis, osteoporosis, dementia, autoimmune disease, and other degenerative diseases of aging. The method combines administration of thioretinamide with enzymatic degradation of homocysteinylated proteins, nucleic acids, and glycosaminoglycans, together with vitamins, amino acids and nitrilosides to enhance metabolic elimination of homocysteine by cystathionine synthase and to promote synthesis of thioretinaco in regenerative cells and measuring and adjusting homocysteine levels to thereby ameliorate the development and progression of degenerative diseases. The compositions include thioretinamide, retinol and combinations thereof with pancreatic enzymes and/or pro-enzymes.

2. Description of Related Art Including Information Disclosed Under 37 CFR 1.97 and 1.98

Abnormal homocysteine metabolism was first implicated in the etiology of degenerative diseases by observation of accelerated arteriosclerosis in children with two different inherited enzymatic disorders resulting from a deficiency of cystathionine synthase and methionine synthase, as reported by McCully K S in *American Journal of Pathology* 1969; 56:111-128. Accelerated arteriosclerosis was subsequently demonstrated in a child with deficiency of methylene tetrahydrofolate reductase, a third enzymatic disorder of homocysteine metabolism, as reported by Kanwar Y S et al in *Pediatric Research* 1976; 10:598-609. In all three of these enzymatic disorders, elevation of blood levels of homocysteine is implicated in the pathogenesis of arteriosclerosis by a direct effect of homocysteine on the metabolic activity of arterial cells and tissues.

Abnormal homocysteine thiolactone metabolism was demonstrated in cultures of cells from malignant tissues, as reported by McCully K S in *Cancer Research* 1976; 36:3198-3202. The results of this study show that cultured malignant cells contain a metabolic blockade of the oxidation of the sulfur atom of homocysteine thiolactone to sulfate, leading to accumulation of homocysteine thiolactone within malignant cells. Homocysteine thiolactone reacts with the free amino groups of macromolecules, forming peptide bonds that cause homocysteinylation of the amino groups of proteins, nucleic acids, and glycosaminoglycans. This metabolic blockade within malignant cells is ascribed to deficiency of a derivative of homocysteine thiolactone that normally occurs within non-malignant cells.

The formation of homocysteine thiolactone from methionine in malignant cells is catalyzed by methionyl t-RNA synthase by an error editing reaction, as reported by Jakubowski H in *FEBS Letters* 1993; 317:237-240. Abnormal homocysteine thiolactone metabolism in malignant cells is hypothesized to result from a deficiency of or a failure to synthesize an N-substituted derivative of homocysteine thiolactone, as discussed in *Cancer Research* 1976; 36:3198-3202. According to this hypothesis, normal cells contain a chemopreventive derivative that facilitates sulfate formation from homocysteine thiolactone. The concentration of this hypothetical derivative is believed to be diminished during the carcinogenic transformation of normal to malignant cells through the action of carcinogenic chemicals, radiation, microbes or chronic inflammation. The function of this chemopreventive derivative in normal cells is to prevent accumulation of homocysteine thiolactone by catalyzing its conversion to phosphoadenosine phosphosulfate, sulfate esters of glycosaminoglycans, steroids, and other compounds, and sulfate ions.

Decreased concentration of this chemopreventive derivative in malignant cells leads to the characteristic metabolic abnormalities of malignancy, which are attributable to excessive accumulation of homocysteine thiolactone. According to this concept, the increased growth rate, the aggregation of nucleoproteins, the increased expression of developmentally suppressed genes, the degradation of cellular membranes, and the abnormalities of oxidative metabolism, such as aerobic glycolysis, are attributable to increased accumulation of homocysteine thiolactone within malignant cells. Treatment of animals with transplanted malignant neoplasms by homocysteine thiolactone perchlorate causes increased necrosis within malignant neoplasms, presumably by increased accumulation of homocysteine thiolactone within malignant tissues, as taught in U.S. Pat. No. 4,255,443.

The identity of the N-substituted derivative of homocysteine thiolactone that prevents growth of malignant tumors in animals was elucidated by organic synthesis of antineoplastic compounds containing homocysteine thiolactone. Arachidonoyl homocysteine thiolactone amide and pyridoxal homocysteine thiolactone enamine decrease the growth of transplanted murine mammary adenocarcinoma, as reported by McCully K S et al in *Chemotherapy* 1977; 23:44-49. As taught in U.S. Pat. No. 4,383,994, N-maleyl homocysteine thiolactone amide, N-maleamide homocysteine thiolactone amide, and rhodium trichloride oxalyl homocysteine thiolactone amide suppress the growth of transplanted neoplasms in animals. Encapsulation of N-maleamide homocysteine thiolactone amide within liposomes greatly enhances its anti-neoplastic activity, as reported by McCully K S et al *in Proceedings of the Society for Experimental Biology and Medicine* 1985; 180:57-61. Structural analysis of these biologically active derivatives of homocysteine thiolactone shows that the hypothetical chemopreventive derivative of homocysteine thiolactone in normal cells is (1) active in a lipid-soluble form, (2) contains a conjugated double bond system with a carbonyl group adjacent to the nitrogen atom of homocysteine thiolactone, and (3) forms a complex with a transition metal atom that enhances anti-neoplastic activity.

U.S. Pat. Nos. 4,618,685 and 4,925,931 teach that the reaction of homocysteine thiolactone with retinoic acid forms N-homocysteine thiolactonyl retinamide (NHTR), known as thioretinamide, and thioretinamide reacts with cobalamin to form N-homocysteine thiolactonyl retinamido cobalamin ((NHTR)$_2$Cbl), known as thioretinaco. Both thioretinamide and thioretinaco have anti-carcinogenic and anti-neoplastic activities, as reported by McCully K S et al in *Carcinogenesis* 1987; 8:1559-1562 and in *Proceedings of the Society for Experimental Biology and Medicine* 1989; 191:346-351. The method of synthesis of thioretinamide was significantly improved by use of N-ethyl-N'-(3-dimethyl-aminopropyl) carbodiimide in the reaction mixture, as taught in U.S. Pat. Nos. 6,054,595 and 6,287,818. This method replaces the conjugation agent, dicyclohexylcarbodiimide in the reaction mixture of the original method and produces pure thioretinamide in 72% of theoretical yield. This pure thioretinamide and its complex with cobalamin, thioretinaco, have anti-atherogenic activity in rats treated with parenteral homocysteine thiolactone, as reported by Kazimir M et al in *Research Communications in Molecular Pathology and Pharmacology* 2002; 5, 6:179-198.

As taught in U.S. Pat. No. 5,565,558 the anti-carcinogenic, anti-neoplastic, anti-viral, and anti-aging activities of thioretinaco ozonide are enhanced by use of membranergic compositions, specifically the polypeptide cytokines, alpha-interferon, beta-interferon, and gamma-interferon. As taught in U.S. Pat. No. 6,696,082 a therapeutically active composition of thioretinaco ozonide for providing anti-carcinogenic, anti-neoplastic, anti-viral, anti-atherogenic, and anti-aging benefits is formed by thioretinaco ozonide, complexed with adenosine triphosphate and oxygen within an ozone-resistant liposomal carrier.

Studies of homocysteine thiolactone metabolism in the liver of scorbutic guinea pigs that are deprived of dietary ascorbate disclosed a failure of oxidation of homocysteine thiolactone to homocysteine and sulfate, as well as a pathway for synthesis of phosphoadenosine phosphosulfate from the sulfur atom of homocysteine thiolactone, as reported by McCully K S in *Nature* 1971; 231:391-392. Homocysteic acid, the oxidized sulfonic acid derivative of homocysteine, promotes growth in normal animals and promotes growth and release of insulin-like growth factor, IGF-1, in hypophysectomized animals that are treated with thyroxine, as reported by Clopath P et al in *Science* 1976; 192:372-374. Young animals and hypophysectomized animals convert more homocysteine thiolactone to homocysteic acid and other oxidized homocysteine derivatives than older or normal animals, as reported by McCully K S in *Annals of Clinical and Laboratory Science* 1975; 5:147-152. Cultured cells that are deficient in cystathionine synthase and unable to convert homocysteine to cystathionine are able to oxidize the sulfur atom of homocysteine thiolactone to sulfate, demonstrating a pathway for sulfate synthesis that is independent of conversion of homocysteine to cystathionine, cysteine and sulfate, as reported by McCully K S in *American Journal of Pathology* 1972; 66:83-95. The pathway for synthesis of sulfate from homocysteine thiolactone involves synthesis of thioretinamide from homocysteine thiolactone and retinoic acid and subsequent oxidation of thioretinamide to sulfite, alpha-keto-butyrate and retinoic acid by superoxide, as described by McCully K S in *Annals of Clinical and Laboratory Science* 1994; 24:27-59.

Nutritional studies have demonstrated that the hyperhomocysteinemia of protein energy malnutrition is associated with reduction in levels of plasma transthyretin, the plasma protein that transports retinol binding protein and thyroxine, as reported by Ingenbleek Y et al in *Nutrition* 2002; 18:40-46. The metabolic disorder caused by protein energy malnutrition involves decreased synthesis and activity of cystathionine synthase, leading to hyperhomocysteinemia and decreased synthesis of cystathionine and cysteine. Transthyretin contains abundant tryptophan, and the plasma level of transthyretin declines in protein energy malnutrition because of dietary deficiency of tryptophan and other essential amino acids, leading to decreased endogenous synthesis of transthyretin. The heme oxygenase function of cystathionine synthase catalyzes the generation of superoxide radical from dioxygen, as reported by Carballal S et al in *Biochemistry* 2008; 47:3194-3202. Retinoic acid enhances the stimulation by thyroid hormone of heme oxygenase activity in the liver of thyroidectomized rats, as reported by Smith J J et al in *Biochimica Biophysica Acta* 1991; 1075:119-122, demonstrating interaction between retinoic acid and the heme group of heme oxygenase. N-(4-hydroxyphenyl)-retinamide, known as fenretinide, induces apoptosis in retinal cells through reactive oxygen species generation and through increased expression of heme oxygenase, as reported by Samuel W et al in *Journal of Cellular Physiology* 2006; 209:854-865. Investigation of fenretinide demonstrates antineoplastic potential, because of its ability to induce apoptosis in malignant cells, as discussed by Hail N Jr et al in *Apoptosis* 2006; 11:1677-1694, and to increase insulin sensitivity in subjects at risk for breast cancer, as discussed by Johannsson et al in *Cancer Research* 2008; 68:9512-9518.

The synthesis of thioretinamide from retinol and homocysteine thiolactone by the heme oxygenase function of cystathionine synthase explains the failure of sulfate synthesis from homocysteine thiolactone in experimental scurvy and the function of dehydroascorbate in sulfate synthesis, as reported by McCully K S in *Nature* 1971; 231:391-392. Thioretinamide is a precursor of thioretinaco by reaction with cobalamin, as taught in U.S. Pat. No. 4,925,931 and reported by McCully K S in *Proceedings of the Society for Experimental Biology and Medicine* 1989; 191:346-351. Thioretinaco ozonide catalyzes the process of oxygen utilization in oxidative phosphorylation, as reported by McCully K S in *Annals of Clinical and Laboratory Science* 1994; 24:27-59. The synthesis of thioretinaco from thioretinamide is facilitated by thyroxine that is transported by plasma transthyretin, explaining how oxidative metabolism is stimulated by thyroxine. Only higher eukaryotes contain cystathionine synthase with a heme functional group, and the cystathionine synthase of prokaryotes, such as yeast and flagellates, contains no heme functional group, as discussed by Miles E W et al in *Journal of Biological Chemistry* 2004; 279:29871-29874. Since embryonic and malignant cells are deficient in the activity of cystathionine synthase, as reported by Kim J et al in *Oncology Reports* 2009; 21:1449-1454, this formulation explains why malignant cells are deficient in oxidation of homocysteine thiolactone to sulfate by the heme oxygenase function of cystathionine synthase.

The embryologist John Beard discovered that trophoblastic cells of the embryo, which invade the uterine endometrium and myometrium during implantation of the fertilized embryo, are related to the asexual cycle of cellular organisms and are converted to placental cytotrophoblastic and syncytiotrophoblastic cells by the action of lytic enzymes produced by the pancreas of the developing fetus. This discovery is described in his book *The Enzymatic Treatment of Cancer and its Scientific Basis*, originally published in 1911, and republished by New Spring Press, New York, 2010 with a foreword by Nicholas Gonzalez. Based on the concept that trophoblastic cells, which are distributed within developing tissues of the fetus, are similar in their cellular behavior to malignant cells, Beard introduced the enzyme treatment of cancer. This treatment consists of injecting enzymes and pro-enzymes extracted from porcine pancreas into patients with various forms of primary or metastatic cancer. The trophoblastic theory of the origin of cancer is based on the assumption that adult stem cells are related to the trophoblastic cells which migrate from the yolk sac of the developing embryo into somatic tissues, as described by Beard.

Human fetal and malignant cells produce small quantities of chorionic gonadotrophin, as reported by Acevedo H F et al in *Cancer* 1995; 76:1467-1475. This hormone is produced in large quantities by the highly malignant tumor of placenta, choriocarcinoma. These observations provide evidence for the trophoblastic origin of malignant cells. Although the origin of adult stem cells in normal human tissues is currently not well understood, the sensitivity of trophoblastic cells to oncolysis by pancreatic enzymes and pro-enzymes forms the theoretical basis for this therapeutic approach, as described by Nicholas Gonzalez and Linda Isaacs in *The Trophoblast and the Origins of Cancer*, published by New Spring Press, New York, 2009. This sensitivity is related to the accumulation of homocysteinylated enzymes, plasma proteins, and cellular proteins by reaction with excess homocysteine thiolactone that accumulates during aging, atherogenesis, carcinogenesis, and autoimmune diseases, as discussed by Perla-Kajan J et al in *Amino Acids* 2007; 32:561-572 and by McCully K S in *Annals of Clinical and Laboratory Science* 1994; 24:27-59.

The enzyme cystathionase (cystathionine γ-lyase) is absent from the liver of human fetus and premature infants, and the activities of the enzymes, cystathionine synthase and adenosyl methionine synthase, are at a level of about 15% to 25% of adult human liver, as reported by Gaull G et al in *Pediatric Research* 1972; 6:538-547. This discovery shows that the transsulfuration pathway for conversion of homocysteine to cystathionine, cysteine and sulfate is inactive in fetal tissues. Therefore, the pathway for synthesis of sulfate from homocysteine thiolactone, involving synthesis of thioretinamide from retinol and homocysteine thiolactone and subsequent oxidation of thioretinamide to sulfite and sulfate by superoxide, is the source of sulfate groups of glycosaminoglycans utilized in the growth of fetal cells and tissues. The fetal cystathionine synthase assayed in human tissues contains the heme oxygenase function of the enzyme, since sulfate groups of glycosaminoglycans and other molecules are synthesized from the sulfur atom of methionine and homocysteine in embryonic tissues.

In the early 20$^{th}$ century the German biochemist Otto Warburg discovered that embryonic tissues and malignant cells are unable to utilize oxygen for cellular metabolism but instead metabolize glucose to lactate as a source of cellular energy, as summarized in Warburg O *Science* 1956; 123:309-314. In other studies, Warburg showed that carcinogenic chemicals decrease normal cellular respiration by inhibition of oxygenases and by inhibition of transport of electrons by cytochrome enzyme systems. These findings are supported by the demonstration of deficient succinic dehydrogenase and cytochrome oxidase activities within malignant tissues, as reported by Schneider et al in *Cancer Research* 1943; 3:353-357.

Taken together these early observations can be interpreted as examples of the clonal selection of malignant cells from trophoblastic stem cells that are deficient in the heme oxidase activity of cystathionine synthase. The resulting failure of oxidation of retinol to retinoic acid and failure of reaction of retinoic acid with homocysteine thiolactone to produce thioretinamide by these malignant cells will lead to deficient formation of thioretinaco and failure of oxidative phosphorylation, catalyzed by thioretinaco ozonide, as discussed by McCully K S in *Annals of Clinical and Laboratory Science* 1994; 24:27-59. The failure of oxidative phosphorylation by malignant cell clones that are deficient in the heme oxygenase function of cystathionine synthase, resulting from decreased production of thioretinaco ozonide from cobalamin and thioretinamide, will lead to an embryonic form of metabolism in which ATP synthesis is dependent upon production of lactate from glucose, otherwise known as aerobic glycolysis.

Nitrilosides are substances containing nitrile groups produced by plants. The most important plant nitriloside is amygdalin (mandelonitrile β-diglucoside), and other nitrilosides are dhurrin (hydroxymandelonitrile β-glucoside), lotaustralin (methylethyl-ketone-cyanohydrin β-glucoside), and linamarin (acetone-cyanohydrin β-glucoside), as discussed in *The Nitrilosides in the Prevention and Control of Cancer*, the McNaughton Foundation, 1962. Malignant cells contain glucosidase, the enzyme that metabolizes amygdalin and other nitrilosides to cyanide. Normal cells contain rhodanese, a sulfotransferase enzyme that catalyzes thiocyanate synthesis from cyanide and hydrogen sulfide. Malignant cells contain insufficient rodanese to prevent accumulation of cyanide. Therefore, the prevention and control of growth of malignant cells and tissues by dietary nitrilosides are attributable to the consequent accumulation of cyanide within malignant cells. The reaction of cyanide with thioretinaco inactivates thioretinaco ozonide, thereby preventing oxidative phosphorylation, as discussed by McCully K S in *Annals of Clinical and Laboratory Science* 2009; 39:219-232. This system of chemical surveillance against the growth of trophoblastic malignant cell clones is promoted by dietary or supplemental consumption of amygdalin and other plant nitrilosides.

Hydrogen sulfide is generated from homocysteine by cystathionine synthase and cystathionase, and low levels of hydrogen sulfide decrease oxidative stress and ameliorate pathological conditions such as ischemia-reperfusion injury, hypertension, and renal failure, as reported by Sen U et al in *American Journal of Physiology Renal Physiology* 2009; 297:F410-F419. Hydrogen sulfide is a key gasotransmitter in sensing oxygen availability in tissues, as discussed by Olson K R in *Antioxidants and Redox Signaling* 2010; 12:1219-1234. The reducing properties of hydrogen sulfide are responsible for scavenging the reactive oxygen species production induced by increased blood levels of homocysteine, inhibiting myocardial injury, as reported by Chang L et al in *Amino Acids* 2008; 34:573-585. Increased production of hydrogen sulfide from homocysteine, metabolized from homocysteinylated proteins, nucleic acids, and glycosaminoglycans of apoptotic cells by pancreatic enzymes will promote catabolism of homocysteine and conversion of the sulfur atom of homocysteine to thiocyanate by reaction of hydrogen sulfide with the cyanide generated from dietary nitrilosides.

During the past 42 years since the discovery of the atherogenic properties of homocysteine in 1969, an elevated level of homocysteine has been demonstrated in the plasma of persons with a wide variety of chronic degenerative diseases. A partial list of these conditions includes arteriosclerosis, stroke, acute coronary syndrome, cancer, osteoporosis and fracture, dementia and other neurodegenerative diseases, autoimmune diseases such as lupus erythematosus, ulcerative colitis, thyroiditis, rheumatoid arthritis and pernicious anemia, venous thrombosis and pulmonary embolism, retinal vein thrombosis, hypothyroidism, accelerated aging, renal failure and uremia, diabetes mellitus, metabolic syndrome, macular degeneration, severe psoriasis, organ transplantation with therapeutic immune suppression, protein energy malnutrition, familial or spontaneous amyloidosis, dietary vitamin deficiencies of folate, pyridoxal, and cobalamin, complications of pregnancy such as pre-ecclampsia and placenta previa, and congenital birth defects, including neural tube defects, cleft palate, and congenital heart disease. The etiology of many of these diseases and conditions is incompletely understood. However, many of these chronic degenerative diseases are strongly correlated with the aging process. The importance of deficiencies of thioretinaco ozonide in cells of aging tissues is discussed by McCully K S in *Annals of Clinical and Laboratory Science* 1994; 24:134-152. Regardless of etiology, however, elevation of plasma homocysteine levels and homocysteinylation of macromolecules in chronic degenerative diseases are susceptible to therapeutic intervention by preservation of cellular oxidative metabolism through increased production of thioretinaco ozonide and by enhanced catabolism of homocysteine produced by enzymatic degradation of homocysteinylated macromolecules. Moreover, preservation of cellular thioretinaco ozonide by membranergic proteins and by the liposomal complex of ATP and oxygen with thioretinaco prolongs survival and counteracts the aging process, as taught in U.S. Pat. Nos. 5,565,558 and 6,696,082.

General aspects of senescence and aging are discussed in *Longevity, Senescence, and the Genome* by Finch C E, University of Chicago Press, Chicago: 1990, pp 380-385. The synthesis of multiple enzymes of liver, muscle and other organs declines with age, and hormonal factors such as corticosteroid hormones are important in restoration of declining enzyme activity with aging. The absorption of folate, pyridoxal and cobalamin, other vitamins and nutrients declines with aging, correlating with decreased production of gastric acid and intrinsic factor, and decreased formation of pancreatic digestive enzymes with aging.

Increasing evidence supports the role of infectious organisms in the pathogenesis of arteriosclerotic plaques. Remnants of infectious microbes, such as *Staphylococcus*, *Streptococcus*, *Salmonella*, Herpes simplex, *Escherichia coli*, *Chlamydia pneumoniae*, *Mycoplasma* pneumonia, *Poryphomonas*, other dental organisms, *Helicobacter pylori*, and Archeae, are detected within plaques by immunohistochemistry, electron microscopy, and hybridization with DNA oligonucleotides directed against microbial nucleic acids. In the case of *Chlamydia pneumoniae*, live organisms have been cultured from plaques. The lipoproteins of the plasma constitute an innate immune system that is capable of inactivating a wide variety of infectious organisms and their toxins by complexation and aggregation. Homocysteine thiolactone reacts with the free amino groups of the apoB protein of low-density lipoproteins to form aggregates that undergo spontaneous precipitation in vitro, as reported by Naruszewicz et al in *Nutrition, Metabolism, and Cardiovascular Disease* 1994; 4:70-77. Vulnerable plaques of arteries in atherosclerosis originate from obstruction of vasa vasorum of arterial wall by aggregates formed from lipoproteins complexed with microbial remnants, homocysteinylated lipoproteins, and lipoprotein autoantibodies in areas of high tissue pressure, causing ischemia, degeneration of arterial wall cells and rupture into arterial intima to form a microabscess, as described by Ravnskov et al in *Annals of Clinical and Laboratory Science* 2009; 39:3-16. The obstruction of vasa vasorum by lipoprotein aggregates is exacerbated by swelling and hyperplasia of endothelial cells, as well as by fibrin deposition in the walls of arterioles, as reported by McCully K S in *American Journal of Pathology* 1969; 56:111-128. These changes in endothelial cell structure and function are manifestations of the endothelial dysfunction caused by hyperhomocysteinemia, as described by McCully K S in *Annals of Clinical and Laboratory Science* 2009; 39:219-232. Increasing evidence also implicates the presence of microbial remnants within the extracellular amyloid plaques and neurofibrillary tangles within neurons as a factor in the pathogenesis of dementia and neurodegenerative diseases, as described by Fife B, in *Stop Alzheimer's Now*, Picadilly Books, Colorado Springs Colo., 2011, pp 115-138.

A number of prior art patents have described methods for measuring homocysteine levels in plasma, cerebrospinal fluid, urine and other body fluids such as, for example, Matsuyama, et al. U.S. Pat. No. 6,686,172, Kawasaki, et al. U.S. Pat. No. 6,867,014 and Esaki, et al. U.S. Pat. No. 7,135,306. The prior art has also recognized that high homocysteine levels are markers for various types of disease. Some of the prior art such as Smith, et al. PCT/US97/20021, Dibner, et al. WO 2006/128048 and Horrobin, et al. U.S. Pub. 2005/0147665 provide methods and compositions for reducing homocysteine levels in mammals having elevated levels of homocysteine. Dibner, et al. WO 2006/128048 uses 2-hydroxy, 4-(thiomethyl) butanoic acid for lowering plasma homocysteine; Smith, et al. PCT/US97/20021 uses B vitamins to lower plasma homocysteine and prevent stroke and Horrobin, et al. U.S. Pub. 2005/0147665 uses an agent selected from a group consisting of vitamin B12, folic acid and vitamin B6. This prior art as well as the previously discussed patented prior art of McCully and Kazimir, et al. have not used pancreatic enzymes together with thioretinamide alone or combined with retinol to facilitate the cellular processing of thioretinamide.

The prior art also includes numerous references to the use of retinol and retinoid compositions as topical treatments for skin such as Millstein Pub. US 2010/0113352, Varani U.S. Pat. No. 6,919,072 and Sin, et al. U.S. Pat. No. 7,030,265 as well as for the treatment of diseases associated with aging. For example Roullet, et al. U.S. Pat. No. 6,437,003 uses retinoids for treating high blood pressure and stroke. The retinol prior art has not used retinol with pancreatic enzyme or has combined retinol with enzymes and thioretinamide to employ the heme oxygenase function of cystathionine synthase to facilitate the cellular processing of thioretinamide and the catabolism of homocysteine.

BRIEF SUMMARY OF THE INVENTION

My invention includes the enhanced endogenic catabolism of homocysteine by measuring homocysteine and decreasing the concentration of homocysteine in the endogenous synthesis of thioretinamide and thioretinaco in tissues and cells. Homocysteine is measured from blood, saliva or other body fluids and is preferably measured from plasma. The endogenous synthesis of thioretinamide and thioretinaco is provided by the administration of an effective amount of thioretinamide or retinol or a combination thereof with pancreatic enzymes and/or pro-enzymes by oral, parenteral or intravenously alone or together with pancreatic enzymes and pro-enzymes to degrade homocysteinated macromolecules.

In one embodiment my invention consists of administration of thioretinamide together with a pancreatic enzyme and/or retinol, by oral, parenteral, or intravenous routes of delivery, combined with pancreatic enzymes and pro-enzymes to degrade homocysteinylated macromolecules, the vitamins folate, pyridoxal, and cobalamin to enhance the activity of cystathionine synthase and methionine synthase, adenosyl methionine to activate cystathionine synthase by allosteric effects, essential amino acids including tryptophan to enhance endogenous transthyretin formation, ascorbate with mixed bioflavonoids to catalyze oxidation of retinol to retinoic acid, and nitrilosides such as amygdalin to provide cyanide to combine with hydrogen sulfide produced by the action of cystathionine synthase and cystathionase on homocysteine and cystathionine, respectively.

In another embodiment my invention encompasses administration of retinol in combination with a pancreatic enzyme by oral, parenteral, or intravenous routes of administration as a metabolic precursor of retinoic acid, in combination with pancreatic enzymes and pro-enzymes, the vitamins folate, pyridoxal and cobalamin, adenosyl methionine, essential amino acids including tryptophan, ascorbate with mixed bioflavonoids, and nitrilosides to facilitate catabolism of homocysteinylated macromolecules and to enhance endogenous synthesis of thioretinamide and thioretinaco. This metabolic program of thioretinamide administration or enhanced endogenous synthesis of thioretinamide and enhancement of homocysteine catabolism will decrease the accumulation of homocysteinylated macromolecules and will decrease the oxidative stress associated with accumulation of homocysteine and inhibition of oxidative metabolism found in human degenerative diseases. In diseases exacerbated by a microbial etiology, such as arteriosclerosis and dementia, use of appropriate antibiotics and triglycerides counteracts microbial growth and inflammation, facilitating the resolution of pathological lesions by the catabolism of homocysteinylated macromolecules by enzyme and metabolic therapy.

In a further embodiment of my invention it has been discovered that an important relationship exists in the cells and tissue between thioretinamide and retinol. Retinol is delivered to cells by the retinol binding protein component of transthyretin, and the heme oxygenase function of cystathionine synthase is responsible for the oxidation of retinol and the simultaneous reaction of retinoic acid with homocysteine thiolactone to produce thioretinamide. This process is catalyzed by binding of dehydroascorbate to the heme group of cystathionine synthase and production of superoxide radical from dioxygen. In catalyzing this reaction of retinol with superoxide radical, dehydroascorbate is simultaneously reduced to semidehydroascorbate, and thioretinamide is formed by the reaction of homocysteine thiolactone with enzyme-bound retinoic acid. These reactions are illustrated as follows:

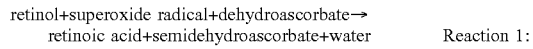

retinol+superoxide radical+dehydroascorbate→
retinoic acid+semidehydroascorbate+water    Reaction 1:

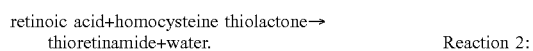

retinoic acid+homocysteine thiolactone→
thioretinamide+water.    Reaction 2:

Thioretinamide is subsequently further metabolized to alph-keto-butyrate, hydrogen sulfide, and retinoic acid, and this pathway is facilitated by oxidation of hydrogen sulfide to sulfite and sulfate by superoxide.

The novel compositions of the invention include thioretinamide or retinol or combinations thereof with pancreatic enzymes or pancreatic pro-enzymes. In the preferred embodiment of the invention the composition includes thioretinamide, retinol together with pancreatic enzymes or pancreatic pro-enzymes. Compositions may also include other compositions that enhance the biosynthesis of thioretinamide and retinol and control methionine and homocysteine catabolism such as dehydroascorbic acid and cobalamin.

Further additional components include adenosyl methionine, pyridoxyl phosphate, n-3 unsaturated oils, tryptophan, mixed essential amino acids, menaquinone, vitamin D3, folate, riboflavin and nicotinic acid.

DETAILED DESCRIPTION OF THE INVENTION INCLUDING BEST MODE

My invention in one embodiment relates to a method for metabolic control of utilization of thioretinamide retinol and combinations thereof with pancreatic enzymes and/or pro-enzymes in prevention and treatment of cancer, arteriosclerosis, dementia, autoimmune disease, and other diseases of aging. These diseases are all characterized by an abnormality of methionine metabolism in which an increased concentration of homocysteine is demonstrated by assaying plasma or other body fluids for homocysteine bound to proteins. The abnormality of methionine metabolism in these diseases is caused by loss or depletion of thioretinamide from the cells of the body. Inadequate oxidation of the retinol of retinol binding protein by the superoxide produced by the heme oxygenase function of cystathionine synthase causes decreased endogenous synthesis of thioretinamide from retinoic acid and homocysteine thiolactone. The resulting decrease in concentration of cellular thioretinamide leads to decreased production of thioretinaco and thioretinaco ozonide from thioretinamide and cobalamin. As a result, oxidative phosphorylation is inhibited because of cellular deficiency of thioretinaco ozonide, leading to accumulation of toxic free radical compounds and producing cellular oxidative stress. In addition, the decreased synthesis of thioretinamide leads to increased production of homocysteine thiolactone from methionine and increased homocysteinylation of the free amino groups of proteins, nucleic acids, glycosaminoglycans and other macromolecules by excess homocysteine thiolactone, impairing cellular function and causing accelerated aging of cells and tissues, as manifested by chronic degenerative diseases of aging.

Human chronic degenerative diseases associated with aging are characterized by oxidative stress produced by un-metabolized free radicals that damage cellular constituents and lead to accumulation of altered proteins within cells and tissues during the disease process. The oxidative stress of these degenerative diseases is produced by the effect of excess metabolic accumulation of homocysteine and homocysteine thiolactone, which interferes with normal oxidative phosphorylation catalyzed by thioretinaco ozonide. My invention overcomes the ineffective metabolic regulation of oxidative stress in human disease of the prior art by a novel method of enhancement of endogenous synthesis of thioretinamide and thioretinaco within cells and tissues, thereby stimulating cellular oxidative metabolism and reducing the endogenous accumulation of reactive oxygen species and reducing the degradation of cellular and tissue constituents by free radical substances in chronic degenerative diseases. My invention also overcomes the overproduction of homocysteine thiolactone by increasing its conversion to cysteine, metabolites of cysteine, and sulfate, preventing the deleterious homocysteinylation of macromolecules that is characteristic of degenerative diseases of aging.

The human chronic degenerative diseases that are benefited by my invention include arteriosclerosis, stroke, acute coronary syndrome, peripheral ischemic gangrene, proliferation of malignant cells in leukemia, lymphoma, sarcoma, carcinoma, and melanoma, osteoporosis and fracture, dementia and other neurodegenerative diseases, autoimmune diseases such as lupus erythematosus, ulcerative colitis, thyroiditis, rheumatoid arthritis and pernicious anemia, venous thrombosis and pulmonary embolism, retinal vein thrombosis, hypothyroidism, accelerated aging, renal failure and uremia, diabetes mellitus, metabolic syndrome, macular degeneration, psoriasis, organ transplantation with therapeutic immune suppression, protein energy malnutrition, familial or spontaneous amyloidosis, dietary deficiencies of folate, pyridoxal, and cobalamin, complications of pregnancy such as pre-ecclampsia and placenta previa, and congenital birth defects, including neural tube defects, cleft palate, and congenital heart disease.

My invention ameliorates the course of these human diseases by preventing accumulation of homocysteine within affected cells and tissues, preventing oxidative stress from free radical accumulation within cells and tissues and preventing accumulation of homocysteinylated macromolecules with impaired function.

The level of homocysteine in plasma increases with age as well as an indication of disease. Risk of disease also increases with age. Table I correlates age and gender with homocysteine levels that as used herein and in the claims are considered a low risk homocysteine level.

TABLE I

Plasma Homocysteine Degenerative Disease Risk Levels

| Disease Risk | Gender | Age | Plasma Homocysteine (µmol/L) |
|---|---|---|---|
| Low | Male | 20-40 | 4-8 |
| Low | Female | 20-50 | 4-8 |
| Mild | Male | 40-60 | 8-12 |
| Mild | Female | 50-60 | 8-12 |
| Moderate | Male | 50-70 | 10-14 |
| Moderate | Female | 60-70 | 10-14 |
| High | Male | 60-80 | 12-20 |
| High | Female | 70-80 | 12-20 |
| Very high | Male | 60-90 | 16-30 |
| Very high | Female | 70-90 | 16-30 |

As demonstrated in Table I, the plasma homocysteine levels vary with age and the risk of degenerative diseases of aging, including vascular disease, neoplastic diseases, autoimmune diseases, osteoporosis and fracture, neurodegenerative diseases, thrombotic diseases, and renal failure, increases with increasing plasma homocysteine levels. Risk increases at an earlier age for males, compared with females of the same age. After menopause, risk increases in females to attain a similar disease risk, compared with males of the same age. In the following Example 1 a 75 year old man with metastatic prostate cancer had a plasma homocysteine level of 14.0 µmol/L, corresponding to moderate to high disease risk; after therapy for six years the homocysteine level was 9.8 µmol/L. In the following Example 2 a 75 year old woman with macular degeneration and cognitive impairment had a plasma homocysteine level of 15.4 µmol/L, corresponding to high disease risk; after therapy for six years the homocysteine level was 8.9 µmol/L. In the following Example 3 a 60 year old man with acute coronary syndrome had a plasma homocysteine level of 15.8 µmol/L, corresponding to high disease risk; after therapy for six years the homocysteine level was 10.5 µmol/L. In the following Example 4 a 65 year old male with metabolic syndrome and early renal failure had a plasma homocysteine level of 16.5 µmol/L, corresponding to very high disease risk; after therapy for six years the homocysteine level was 10.2 µmol/L. In the following Example 5 a 70 year old man with arteriosclerosis and aortic aneurysm had a plasma homocysteine level of 18.5 µmol/L, corresponding to very high disease risk; after therapy for six years the homocysteine level was 10.8 µmol/L. In the following Example 6 a 65 year old woman with stroke had a plasma homocysteine level of 18.0 µmol/L, corresponding to very high disease risk; after therapy for six years the homocysteine level was 10.5 mol/L.

Thioretinamide, also known as N-homocysteine thiolactonyl retinamide (NHTR), can be prepared, as described in U.S. Pat. Nos. 4,618,685, 6,054,595, and 6,287,818 by the reaction of homocysteine thiolactone with retinoic acid. Thioretinaco, also known as N-homocysteine thiolactonyl retinamido cobalamin ((HTHR)$_2$Cbl), can be prepared, as described in U.S. Pat. No. 4,925,931, by reaction of thioretinamide with 5'-deoxyadenosyl cobalamin (Cbl). Thioretinaco ozonide ((NTHR)$_2$CblO$_3$) can be prepared, as described in U.S. Pat. No. 5,565,558 by reaction of ozone with thioretinaco. Preservation of cellular thioretinaco ozonide by membranergic proteins and by a liposomal complex of ATP and oxygen with thioretinaco ozonide prolongs survival and counteracts the aging process, as taught in U.S. Pat. Nos. 5,565,558 and 6,696,082. As used herein and in the claims thioretinamide will be referred to as thioretinamide to include N-homocysteine thiolactyl retinamide (NHTR), thioretinaco or N-homocysteine thiolactonyl retinamido cobalamin ((HTHR$_2$)cbl) and thioretinaco ozonide ((NHTR)$_2$cblo$_3$).

The specific and essential components of my invention comprise a metabolic program of delivering effective amounts of thioretinamide, retinol and combinations thereof with pancreatic enzymes or pro-enzymes by oral, intravenous or parenteral routes of administration. The program consists of (1) synthetic thioretinamide or dietary retinol as a precursor to endogenous thioretinamide synthesis; (2) ascorbate with bioflavonoids to promote oxidation of retinol to retinoic acid by dehydroascorbate and synthesis of thioretinamide from homocysteine thiolactone, catalyzed by the heme oxygenase function of cystathionine synthase; (3) cobalamin as a precursor of endogenous thioretinaco synthesis, formed from thioretinamide and catalyzed by cystathionine synthase; (4) adenosyl methionine and pyridoxal phosphate to activate cystathionine synthase; (5) amygdalin to serve as a precursor of cyanide for reaction with hydrogen sulfide to produce thiocyanate; (6) n-3 unsaturated oils to lower blood homocysteine levels; (7) pancreatic porcine enzymes and pro-enzymes to catabolize homocysteinylated proteins, nucleic acids and glycosaminoglycans; (8) tryptophan and mixed essential amino acids to promote synthesis of transthyretin; (9) menaquinone to prevent dystrophic calcification; (10) vitamin D3 to stabilize mitochondrial thioretinaco ozonide; (11) folate to provide a substrate for synthesis of methyltetrahydrofolate, the coenzyme for synthesis of methyl cobalamin and methylation of homocysteine to methionine; (12) riboflavin as a precursor to methylenetetrahydrofolate reductase to catalyze synthesis of methyltetrahydrofolate and methylcobalamin for methylation of homocysteine to methionine; (13) vitamers of the vitamin B family including nicotinic acid as precursors to nicotinamide adenine dinucleotide, the catalyst for dehydrogenation reactions; (14) dietary modification to eliminate processed foods and alcohol and to increase consumption of nitrilosides, proteins containing methionine, and organic sulfur compounds to convert endogenous hydrogen sulfide to thiocyanate by reaction with endogenous cyanide, facilitating homocysteine catabolism by trans-sulfuration of homocysteine to cysteine and cysteine catabolites; (15) broad spectrum antibiotics to eliminate intracellular micro-organisms associated with arteriosclerotic plaques and cerebral amyloid deposition; and (16) consumption of medium chain saturated triglycerides with anti-microbial activity.

The required doses of the components in accordance with the best mode of my invention are exemplified in Examples 1 through 6. However, my invention is effective over a wide range of dosage of thioretinamide, depending upon the stage and severity of the degenerative disease under treatment. The dose of thioretinamide is effective over a broad range of concentrations, from 7.5 mg/70 kg/day to 300 mg/70 kg/day. Subjects with severe disease risk and symptoms are conveniently treated with a high dose of thioretinamide, 300 mg/70 kg/day, for a period of one to six months in order to halt the progression of disease. Subjects with moderate disease risk and symptoms are conveniently treated with a moderate dose of thioretinamide, 75 mg/70 kg/day, to control symptoms of disease, and subjects with low risk of disease are conveniently treated with a low dose of thioretinamide, 7.5 mg/70 kg/day, to maintain health without disease over a period of years. Thioretinamide can also be used in combination with retinol over a wide range of dosage and over a wide range of relative amounts of the two compounds. Subjects with high disease risk and symptoms are conveniently treated with a high ratio of thioretinamide to retinol, varying from 100:1 to 1:1 on a molar basis. Subjects with low or moderate disease risk and symptoms are conveniently treated with a lower ratio thioretinamide to retinol, varying from 1:1 to 1:100 on a molar basis. Retinol can be used effectively as a substitute for thioretinamide in subjects with a low to moderate disease risk over a wide range of dosage, varying from 7.5 mg/70 kg/day to 300 mg/70 kg/day. These wide dose ranges of thioretinamide and retinol, varying from 7.5 mg/70 kg/day to 300 mg/70 kg/day, as used in my invention, are associated with no evidence of toxicity, such as weight loss, nausea, impairment of liver function, headache, or skin lesions, in animal tests or in human trials.

The dosage of pancreatic enzymes and pro-enzymes in accordance with the best mode of my invention, as exemplified in Examples 1 through 6, is effective over a range of concentrations, varying from 1.4 g/70 kg/day to 14 g/70 kg/day. Subjects with high risk of disease benefit from the higher dose range, and subjects with low risk of disease or on maintenance therapy benefit from the lower dose range. The relative ratios of pancreatic enzyme dose to thioretinamide dose or retinol dose are effective over a wide range, varying from 1.4 g/70 kg/day to 14 g/70 kg/day of enzymes, from 7.5 mg/70 kg/day to 300 mg/70 kg/day for thioretinamide, and from 7.5 mg/70 kg/day to 300 mg/70 kg/day for retinol. The doses of the vitamins, amino acids, nitrilosides, n-3 unsaturated oils, broad spectrum antibiotics, and medium chain saturated triglycerides of my invention are similarly effective over a range of dosage, as exemplified in Examples 1 through 6. The following ranges of doses of these components of my invention are useful for controlling disease risk by my invention: ascorbate, 0.1 to 10 g/70 kg/day; cobalamin 0.01 to 1 mg/70 kg/day; adenosyl methionine, 0.1 to 1.0 g/70 kg/day; pyridoxal, 2.0 to 200 mg/70 kg/day; amygdalin, 0.1 to 10 g/70 kg/day; n-3 unsaturated oils, 1.0 to 20 g/70 kg/day; tryptophan and mixed essential amino acids, 0.1 to 1.0 g/70 kg/day; menaquinone, 0.01 to 1.0 mg/70 kg/day; vitamin $D_3$, 100 to 2000 IU/70 kg/day; folate, 0.2 to 2.0 mg/70 kg/day; riboflavin 1.0 to 50 mg/70 kg/day; nicotinic acid, 1.0 to 50 mg/70 kg/day; broad spectrum antibiotics such as doxycycline, 0.1 to 5.0 g/70 kg/day; medium chain saturated triglycerides, 1.0 to 10 g/70 kg/day. In accordance with the best mode of the invention pharmaceutical preparations of thioretinamide or retinol or combinations thereof along with a pancreatic enzyme are formulated from about 0.05% to 21.4% weight percent (wt %) of thioretinamide, retinol or combinations thereof to about 97.9% to 99.5% weight percent (wt %) of pancreatin. To this core pharmaceutical preparation other compounds may be added including broad spectrum antibiotics, amino acids, bioflavonoids, adenosyl methionine, vitamins as well as other components specific to treatment of a specific disease or a degenerative disease of aging.

The novel method for utilization of thioretinamide by the metabolic program embodied in this invention is useful for prevention of induction of malignant neoplasms and for treatment of primary and metastatic neoplasms in human subjects exposed to carcinogenic chemicals, radiation or oncogenic microbes, causing regression of malignant cell proliferation. The method of this invention is also useful in prevention and regression of arteriosclerotic plaques of aorta and peripheral arteries in human subjects exposed to an atherogenic diet and multiple infections of the plaques by micro-organisms. The method of this invention is also useful in prevention of the replication of pathogenic viruses to prevent or cause regression of the pathogenic effects of these viruses and to prevent post-infection sequelae of these viruses. The method of this invention is also useful in preventing the degenerative aging changes of their tissues, decreased oxidative metabolism, and decreased life expectancy associated with aging by prevention of further degenerative changes of tissues associated with aging, by enhancement of oxidative metabolism, and by prolongation of life span. In this respect the method of my invention is non-toxic and does not suffer the drawback of many known antineoplastic, antiatherogenic, antiviral, and antiaging agents, which have cumulative toxic effects after prolonged administration.

Currently available therapies for acute coronary syndrome are not totally effective in preventing recurrent vascular disease events. Current therapies with anti-platelet agents, beta-blockers, anticoagulants, thromboplastin activators, calcium channel inhibitors, and angiotensin converting enzyme inhibitors are only partially effective in therapy. Treatment of hyperhomocysteinemia with pyridoxal, folate and cobalamin does not prevent recurrence of adverse events in subjects with advanced cardiovascular, cerebrovascular, or peripheral vascular disease. Treatment of human subjects with the method of my invention will correct the underlying metabolic abnormality leading to acute coronary syndrome and other forms of vascular disease by restoring depleted concentrations of thioretinamide and thioretinaco ozonide within mitochondrial membranes of vascular cells, restoring endothelial function, preventing a prothrombotic state, and restoring nitric oxide function. The hyperhomocysteinemia that is characteristic of acute coronary syndrome, metabolic syndrome and chronic arteriosclerosis will be prevented by restoration of mitochondrial thioretinaco ozonide, preventing vascular injury, endothelial dysfunction, progression of arteriosclerotic plaques, and recurrent vascular events, such as coronary thrombosis, myocardial infarction, cerebrovascular thrombosis, cerebral infarction, and ischemic gangrene of the extremities.

The novel method of utilization of thioretinamide of my invention is deemed useful in preventing the occurrence of spontaneous human neoplasms, including, but not limited to, cancer of lung, skin, colon, breast, prostate, pancreas, brain, lymph nodes, liver, kidney or other organs that arise because of exposure to carcinogenic chemicals, electromagnetic radiation, radiation from radioactive elements, viruses, micro-organisms, inflammatory cytokines, dietary factors, or genetic factors. My invention is further deemed useful for the treatment of human neoplasms, causing regression of or preventing metastasis of malignant neoplasms. It is also deemed that this invention is useful in treatment of human atherosclerosis, involving aorta, coronary, renal, peripheral, cerebral or other major arteries, causing regression of and prevention progression of arteriosclerotic plaques, thereby preventing or ameliorating coronary heart disease, stroke, renovascular disease, and peripheral vascular disease.

My invention is also deemed useful in treatment of human pathogenic virus infections, including, but not limited to hepatitis virus, immune-deficiency virus, hemorrhagic fever viruses, encephalitis viruses, influenza virus, rhinoviruses, pox viruses, herpetic viruses, and enteric viruses, by preventing viral replication and spread of the virus infection within the cells of the various tissues of the body. My invention is also deemed useful in treatment of human degenerative diseases associated with aging, including, but not limited to, osteoarthritis, osteoporosis, cataract, macular degeneration, dementia, diabetes mellitus, metabolic syndrome, rheumatoid arthritis, thyroiditis, lupus erythematosus, pernicious anemia, and other autoimmune disorders, causing remission or preventing of progression of these diseases within the tissues of the body. It is expected that my invention will be useful in prolonging human life span by preventing degenerative diseases of aging, including atherosclerosis, cancer, autoimmune diseases, and age-associated loss of function of brain, heart, lungs, liver, kidneys, eyes, ears, and other major organs.

The range of useful concentrations of thioretinamide is broad, extending from 0.1-60 mg/kg of body weight. The subject invention can be administered to human subjects in the aforesaid dosage range. Suspensions, emulsions and dispersions of thioretinamide can be administered by the enteric route, employing capsules and protective coatings along with time-release formulations, mixed with suitable inert carriers. The subject invention can also be administered parenterally in compatible solvents and vehicles, given intravenously, intramuscularly, introperitoneally, subcutaneously, intracisternally, intrathecally, and within neoplasms in various internal organs by direct injection, with ultrasound, nuclear magnetic resonance, or X-ray computerized tomography guidance. The administration of thioretinamide is combined with the other supportive measures, previously enumerated, to maximize the therapeutic efficacy of the treatments.

It will be understood by those skilled in the art that the actual preferred amount of thioretinamide used will vary according to the specific isomer being used, the particular compositions formulated, the mode of application and particular site and subject being treated. Optimal application rates for a given set of conditions can be ascertained by those skilled in the art, using conventional dosage determination tests in accordance with the detailed description of this invention.

The advantages of the invention, as well as aspects of the preferred embodiments, are illustrated in the following Examples which demonstrate the administration of synthetic thioretinamide or retinol with enzymes are effective in treating degenerative diseases associated with aging by measuring and reducing homocysteine. The following Examples are illustrative only and not for limiting the scope of applicability of the invention.

EXAMPLE 1

A 75 year old man was evaluated for treatment of metastatic prostate cancer. Five years previously the prostate specific antigen (PSA) of blood was determined at 8.0 ng/mL, and needle biopsy demonstrated well differentiated adenocarcinoma, Gleason grade 3+3=6/10. Following radical prostatectomy, the PSA value was 0.1 ng/mL and gradually increased to 8.0 ng/mL over a period of 5 years. The plasma homocysteine was initially 10.8 µmol/L, gradually rising to 14.0 µmol/L over a period of 5 years. Computerized tomography scan demonstrated enlarged retroperitoneal lymph nodes, and biopsy of the prostatic surgical site demonstrated recurrent adenocarcinoma. The bone scan revealed no evidence of metastasis. Following luprolide therapy, the PSA value declined to 0.1 ng/mL over a period of three months. To prevent metastasis and hormone resistance of the adenocarcinoma, luprolide therapy was discontinued and a metabolic program was employed. The oral medications and supplements consisted of synthetic thioretinamide, 75 mg per day; pancreatin, 1.4 g four times per day; amygdalin, 500 mg per day; adenosyl methionine, 200 mg per day; pyridoxal phosphate, 25 mg per day; cyanocobalamin, 500 µg sublingual per day; ascorbate with mixed bioflavonoids, 1000 mg per day; folic acid, 800 µg per day; riboflavin, 25 mg per day; nicotinic acid, 125 mg per day; menoquinone, 90 µg per day; vitamin $D_3$, 2000 units per day; fish oil, 3 g per day; cod liver oil, 15 mL per day; tryptophan 500 mg per day; mixed amino acids 150 mg each per day. The diet was adjusted to eliminate all processed foods containing sugar, white flour, powdered milk, powdered eggs, protein hydrolyzates, natural flavoring extracts, and alcohol. Dietary consumption of berries, nuts, apricot seeds, beans, molasses, fruits, raw vegetables, steamed vegetables, fish and fresh meats was increased. After following the metabolic program for one year the PSA value was 0.1 ng/mL, the plasma homocysteine was 10.4 µmol/L, and the repeat CT scan and bone scan showed no evidence of lymphadenopathy or bone metastasis. At a subsequent visit 5 years later, the PSA value was 0.1 ng/mL, the plasma homocysteine was 9.8 µmol/L, and no weight loss or pain were reported, while continuing the metabolic program.

EXAMPLE 2

A 75 year old woman was evaluated for treatment of macular degeneration and mild recent memory loss. Three years previously decreased vision was noticed in the left eye, and ophthalmological evaluation revealed early supranuclear cataracts bilaterally with edema of the macular area on the left, associated with drusen and retinal pigment epithelium changes. The plasma homocysteine level was 15.4 µmol/L, and the plasma hs-C-reactive protein (CRP) was 3.2 µmol/mL. The Mini Mental State Examination (MMSE) value was 26.6/30, revealing mild cognitive impairment. The woman never smoked, but there was a family history of macular degeneration. After 3 years, she returned with decreased vision in the right eye, and examination revealed macular edema associated with drusen and retinal pigment epithelium changes. Dental examination revealed caries, plaque, and extensive peri-odontitis. To prevent progression of macular changes and decline in mental function, a metabolic program was employed. The oral medications and supplements consisted of retinol, 20,000 IU per day as synthetic retinol or from cod liver oil, 15 mL per day; pancreatin, 1.4 g four times per day; amygdalin, 100 mg per day; adenosyl methionine, 200 mg per day; pyridoxal phosphate, 25 mg per day; cyanocobalamin, 500 µg sublingual per day; ascorbate with mixed bioflavonoids, 1000 mg per day; folic acid, 800 µg per day; riboflavin, 25 mg per day; nicotinic acid, 125 mg per day; menoquinone, 90 µg per day; vitamin D3, 2000 IU per day; fish oil, 3 g per day; tryptophan, 500 mg per day; mixed amino acids, 150 mg each per day; monolaurin, as coconut oil, 60 g per day; doxycycline, 100 mg per day. The diet was adjusted to eliminate all processed foods containing sugar, white flour, powdered milk, powdered eggs, protein hydrolyzates, natural flavoring extracts, and alcohol. Dietary consumption of berries, nuts, beans, molasses, fruits, raw vegetables, steamed vegetables, fish and fresh meats was increased. Professional dental hygiene was provided every 3 months. After following the metabolic program for one year, the plasma homocysteine was 10.7 µmol/L, and the CRP was 0.5 µmol/mL. The repeat MMSE was 28.5/30. Visual acuity did not change, and examination revealed decreased macular edema bilaterally. Improved memory was reported by her husband. At a subsequent visit 5 years later, the plasma homocysteine was 8.9 µmol/L, the CRP was less than 0.5 µmol/mL, the MMSE was 28.0/30, the visual acuity and macular appearance were unchanged, while continuing the metabolic program.

EXAMPLE 3

A 60 year old man was admitted to hospital with intermittent chest pain and shortness of breath. The man was diaphoretic and restless with acute distress. The troponin was 1.5 ng/mL, the white blood cell count was 15,000/mm$^3$, the plasma homocysteine was 15.8 µmol/L, and the CRP was 7.5 µmol/mL. The electrocardiogram demonstrated ST elevation in the precordial leads. A chest X-ray showed early pulmonary edema and congestion of pulmonary arteries. Dental examination revealed caries, plaque and extensive peri-odontitis. After treatment with pain medication, bed rest, and digoxin, the electrocardiogram reverted to normal, his symptoms improved, and a metabolic program was employed. The oral medications and supplements consisted of synthetic thioretinamide, 75 mg per day; pancreatin, 1.4 g four times per day; amygdalin, 500 mg per day; adenosyl methionine, 200 mg per day; pyridoxal phosphate, 25 mg per day; cyanocobalamin, 500 µg sublingual per day; ascorbate with mixed bioflavonoids, 1000 mg per day; folic acid, 800 µg per day; riboflavin, 25 mg per day; nicotinic acid, 125 mg per day; menoquinone, 90 µg per day; vitamin D$_3$, 2000 units per day; fish oil, 3 g per day; cod liver oil, 15 mL per day; tryptophan 500 mg per day; mixed amino acids 150 mg each per day; monolaurin, as coconut oil, 60 g per day; doxycycline, 100 mg per day. The diet was adjusted to eliminate all processed foods containing sugar, white flour, powdered milk, powdered eggs, protein hydrolyzates, natural flavoring extracts, and alcohol. Dietary consumption of berries, nuts, beans, molasses, fruits, raw vegetables, steamed vegetables, fish and fresh meats was increased. Professional dental hygiene was provided every 3 months. After following the metabolic program for one year, the plasma homocysteine was 9.8 µmol/L, the CRP was 0.5 µmol/mL, and the troponin was undetectable. There was no recurrence of chest pain, and the electrocardiogram was normal. At a subsequent visit 5 years later the plasma homocysteine was 10.5 µmol/L, the CRP was less than 0.5 µmol/L, the troponin was undetectable, the electrocardiogram was normal, and there was no recurrence of chest pain, while continuing the metabolic program.

EXAMPLE 4

A 65 year old male was evaluated for treatment of obesity, hypertension, and elevated blood glucose. During the previous 5 years, gradual weight gain involved abdominal viscera with a protuberant abdomen, the girth increasing to 44 inches. The blood pressure was 180 systolic and 110 diastolic. The plasma homocysteine was 16.5 union, the fasting blood glucose was 125 mg/dL, the urinalysis revealed microalbuminuria of 2.5 mg/dL, and the plasma creatinine was 2.0 mg/dL. To prevent progression of the metabolic syndrome and early renal failure, dietary improvement, moderate exercise, and a metabolic program were employed. The oral medications and supplements consisted of retinol, 20,000 units, as synthetic retinol or from cod liver oil, 15 mL per day; pancreatin, 1.4 g four times daily; amygdalin, 100 mg per day; adenosyl methionine, 200 mg per day; pyridoxal phosphate, 25 mg per day; cyanocobalamin, 500 µg sublingual per day; ascorbate with mixed bioflavonoids, 1000 mg per day; folic acid 800 µg per day; riboflavin, 25 mg per day; nicotinic acid, 125 mg per day; menoquinone, 90 µg per day; vitamin D3, 2000 IU per day; fish oil, 3 g per day; tryptophan, 500 mg per day; mixed amino acids, 150 mg each per day; monolaurin, as coconut oil, 60 g per day. The diet was adjusted to eliminate all processed foods containing sugar, white flour, powdered milk, powdered eggs, protein hydrolyzates, natural flavoring extracts, and alcohol. Dietary consumption of berries, nuts, beans, molasses, fruits, raw vegetables, steamed vegetables, fish and fresh meats was increased. Moderate exercise, consisting of a 1.5 mile walk three days per week, and doubles tennis once per week were employed. After following the dietary adjustment, exercise program and metabolic program for one year, the plasma homocysteine was 11.0 µmol/L, the fasting blood glucose was 98 mg/dL, the urinalysis revealed no protein, and the plasma creatinine was 1.5 mg/dL. Weight loss of approximately 15 pounds was reported, and the abdominal girth measured 41 inches. The blood pressure was 140 systolic and 85 diastolic. At a subsequent visit 5 years later, additional weight loss of 10 pounds and a girth of 40 inches were reported, while continuing the metabolic program. The plasma homocysteine was 10.2 µmol/L, blood glucose was 95 mg/dL, the urinalysis revealed no protein, and the plasma creatinine was 1.7 mg/dL. The blood pressure was 140 systolic and 85 diastolic.

EXAMPLE 5

A 70 year old man with mild abdominal pain was evaluated for treatment of an abdominal aortic aneurysm that was detected by computerized tomography. On examination, a 1 cm ulcer was found on the right great toe. The patient reported the onset of pain in the lower extremities after walking approximately 50 yards. The plasma homocysteine was 18.5 µmol/L, the CRP was 10.7 µmol/mL, and the fasting blood glucose was 98 mg/dL. Dental examination revealed caries, plaque, and extensive peri-odontitis. Surgical treatment consisted of excision of the abdominal aortic aneurysm with grafting of the distal aorta, followed by endarterectomy of the right common femoral artery with grafting. The pathology report confirmed the presence of an arteriosclerotic aortic aneurysm, with laminated mural thrombus, and inflammatory changes of the adventitia. Also, fibrocalcific arteriosclerotic plaques were found in the common femoral artery with severe narrowing of the lumen. After recovery from surgery, the ulceration of the great toe gradually healed spontaneously. To prevent progression of generalized arteriosclerosis, a metabolic program, dietary adjustment, and antibiotic therapy were employed. The oral medications and supplements consisted of synthetic thioretinamide, 75 mg per day; pancreatin, 1.4 g four times per day; amygdalin, 100 mg per day; adenosyl methionine, 200 mg per day; pyridoxal phosphate, 25 mg per day; cyanocobalamin, 500 μg sublingual per day; ascorbate with mixed bioflavonoids, 1000 mg per day; folic acid 800 μg per day; riboflavin, 25 mg per day; nicotinic acid, 125 mg per day; menoquinone, 90 μg per day; vitamin $D_3$, 2000 IU per day; fish oil, 3 g per day; cod liver oil, 15 mL per day; tryptophan, 500 mg per day; mixed amino acids, 150 mg each per day; monolaurin, as coconut oil, 60 g per day; doxycycline, 100 mg per day. The diet was adjusted to eliminate all processed foods containing sugar, white flour, powdered milk, powdered eggs, protein hydrolyzates, natural flavoring extracts, and alcohol. Dietary consumption of berries, nuts, beans, molasses, fruits, raw vegetables, steamed vegetables, fish and fresh meats was increased. Professional dental hygiene was provided every 3 months. After following the dietary adjustment and metabolic program for one year, the plasma homocysteine was 12.5 μmol/L, the CRP was 1.5 μmol/mL, and the fasting blood glucose was 95 mg/dL. There was no recurrence of the ulcer of the great toe, and there were no symptoms of intermittent claudication. At a subsequent examination 5 years later, the plasma homocysteine was 10.8 μmol/L, the CRP was 1.2 μmol/mL, and the fasting blood glucose was 95 mg/dL. There were no further symptoms of abdominal pain, skin ulcers or intermittent claudication, while following the metabolic program.

EXAMPLE 6

A 65 year old woman was evaluated for the sudden onset of right sided weakness, associated with inability to speak and difficulty seeing objects in the right visual field. The plasma homocysteine was 18.0 μmol/L, the CRP was 12.5 μmol/mL, and the fasting blood glucose was 102 mg/dL. Following thrombolytic therapy for stroke, her symptoms gradually improved while convalescing at home. After recovering for 3 months, she tripped on a rug and fell, fracturing the right femoral neck. After surgical fixation of the fracture, she was evaluated for osteoporosis that was demonstrated on the X-rays of her fracture site and spine. To prevent further episodes of cerebrovascular disease and fracture, dietary adjustment and a metabolic program were employed. The oral medications and supplements consisted of synthetic thioretinamide, 75 mg per day; pancreatin, 1.4 g four times per day; amygdalin, 100 mg per day; adenosyl methionine, 200 mg per day; pyridoxal phosphate, 25 mg per day; cyanocobalamin, 500 μg sublingual per day; ascorbate with mixed bioflavonoids, 1000 mg per day; riboflavin, 25 mg per day; nicotinic acid, 125 mg per day; menoquinone, 90 μg per day; vitamin $D_3$, 2000 IU per day; fish oil, 3 g per day; cod liver oil, 15 mL per day; tryptophan, 500 mg per day; mixed amino acids, 150 mg each per day; monolaurin, as coconut oil, 60 g per day; doxycycline, 100 mg per day. The diet was adjusted to eliminate all processed foods containing sugar, white flour, powdered milk, powdered eggs, protein hydrolyzates, natural flavoring extracts, and alcohol. Dietary consumption of berries, nuts, beans, molasses, fruits, raw vegetables, steamed vegetables, fish and fresh meats was increased. After following the dietary adjustment and metabolic program for one year, the plasma homocysteine was 12.5 μmol/L, the CRP was 4.5 μmol/mL, and the fasting blood glucose was 86 mg/dL. The hemiparesis and visual field defects were no longer demonstrated. There were no further episodes of mental changes, visual disturbances, or weakness. The hip prosthesis was satisfactory, permitting full ambulation. At a subsequent evaluation after 5 years, the plasma homocysteine was 10.5 μmol/L, the CRP was 0.5 μmol/mL, and the fasting blood glucose was 85 mg/dL. There were no further symptoms of weakness, visual disturbances, or mental changes, and ambulation was satisfactory, while following the metabolic program.

My invention provides a method and compositions to enhance thioretinamide utilization and homocysteine catabolism, consisting of oral, parenteral or intravenous administration of thioretinamide or retinol or combinations thereof together with enzymes or pro-enzymes. In the best mode the invention includes the administration of effective amounts of thioretinamide or retinol or combinations thereof to a mammal in need thereof together with enzymes and pro-enzymes. In the best mode pancreatic enzymes and pro-enzymes are used with thioretinamide or retinol or combinations thereof alone or in combination with folate, pyridoxal phosphate and cobalamin; adenosyl methionine; essential amino acids including tryptophan; ascorbate with mixed bioflavonoids; nitrilosides, including but not limited to amygdalin, dhurrin, linamarin, lotaustralin; n-3 unsaturated oils; monolaurin; and antibiotics, for the purpose of ameliorating the progression of human degenerative diseases of aging, including but not limited to cancer, arteriosclerosis, acute coronary syndrome, stroke, ischemic gangrene, osteoporosis and fracture, dementia and other neurodegenerative diseases, autoimmune diseases, including but not limited to lupus erythematosus, ulcerative colitis, thyroiditis, rheumatoid arthritis, and pernicious anemia, thrombosis and embolism, retinal vein thrombosis, macular degeneration, hypothyroidism, accelerated aging, renal failure and uremia, diabetes mellitus, metabolic syndrome, protein energy malnutrition, familial or spontaneous amyloidosis, dietary vitamin deficiencies, complications of pregnancy, including but not limited to pre-ecclampsia and placenta previa, and congenital birth defects, including but not limited to neural tube defects, cleft palate and congenital heart disease.

My invention may be modified by those skilled in the art in a number of different ways for specific applications due to its broad range of applications. The range of applicability is related to the specific treatment as well as the constituents needed for the biosynthesis of thioretinamide, thioretinaco and thioretinaco ozonide and the catabolism of homocysteine resulting from the enzymatic action of pancreatic enzymes from compositions formulated in accordance with my invention which include thioretinamide, retinol and combinations thereof with a pancreatic enzyme.

The compositions formulated in accordance with my invention are enhanced by dietary or added constituents that control methionine and homocysteine metabolism. The constituents include adenosyl methionine, pyridoxyl phosphate, n-3 unsaturated oils, cyanocobalamin, tryptophan, mixed essential amino acids, menaquinone, vitamin D3 or cholecalciferol, folate, riboflavin, nicotinic acid and amygdalin. The pancreatic enzymes and pro-enzymes catabolize the macromolecules containing homocysteine into cysteine, cysteine metabolates and sulfates. This process is enhanced by pyridoxyl phosphate and adenosyl methionine. Adenosyl methionine may be used or its stable salts including tosylate, butanedisulfonate, disulfate tosylate, disulfate ditosylate and disulfate monotosylate.

The process of my invention includes the use of additional biochemical markers in addition to plasma homocysteine. These biochemical markers include C-reactive protein (CRP) prostate specific antigen (PSA) or additional more related markers depending upon the disease under consideration. For example, C-reactive protein is an acute phase reactant of plasma produced by the liver in infections or other inflammatory conditions. Transthyretin is a plasma protein that is sensitive to protein malnutrition and transports thyroid hormone and retinol to cells and tissues. Bioflavonoids provide an anti-oxidant function while menaquinone or vitamin K2 is needed for calcium metabolism to prevent dystrophic calcification of arterial plaques and other tissues. It is to be understood that those skilled in the art will adapt and modify my invention for specific applications and that such applications are within the spirit and scope of the invention.

My invention is useful in therapy of human diseases characterized by impairment of utilization of thioretinamide and homocysteine catabolism, as reflected in elevation of blood homocysteine concentrations. While the foregoing Examples, Table and description has included specific formulations and details of the method it is understood that modifications and changes will be made by those skilled in the art for specific conditions and treatments without departing from the broad applicability and scope of the disclosure. It is to be understood that those skilled in the art will make changes and modifications of my invention to adapt it to various usages and conditions that are within the full scope of the appended claims and their equivalents.

I claim:

1. A composition of matter for the catabolism of homocysteine in tissues and cells comprising a therapeutically effective amount of thioretinamide and a therapeutically effective amount of pancreatin and optionally a therapeutically effective amount of retinol.

2. The composition of claim 1 wherein said formulation does not comprise retinol.

3. The composition of claim 2 wherein said formulation is from about 0.05% to 21% wt % of thioretinamide to about 97% to 99.5% wt % of pancreatin.

4. The composition of claim 3 further comprising a therapeutically effective amount of adenosyl methionine or the salts thereof.

5. The composition of claim 3 further comprising a therapeutically effective amount of a vitamin or a pro vitamin.

6. The composition of claim 5 wherein said vitamin or pro-vitamin is vitamin C or an ascorbate.

7. The composition of claim 6, wherein said composition further includes a therapeutically effective amount of a bioflavonoid.

8. The composition of claim 5 wherein said vitamin is a vitamer of the B family.

9. The composition of claim 8 wherein said vitamer is pyridoxal phosphate.

10. The composition of claim 8 wherein said vitamer is cyanocobalamin.

11. The composition of claim 8 wherein said vitamer is amygdalin.

12. The composition of claim 8 wherein said vitamer is a tolate or folic acid.

13. The composition of claim 8 wherein said vitamer is nicotinic acid.

14. The composition of claim 8 wherein said vitamer is riboflavin.

15. The composition of claim 2 further comprising a therapeutically effective amount of an amino acid.

16. The composition of claim 15 wherein said amino acid is tryptophan.

17. The composition of claim 2 further comprising a therapeutically effective amount of a broad spectrum antibiotic.

18. The composition of claim 17 wherein said broad spectrum antibiotic is doxycycline.

19. The composition of claim 1 wherein said formulation comprises thioretinamide, pancreatin and retinol.

20. A method of catabolizing homocysteine in a human comprising:
    (a) measuring the concentration of homocysteine in a body fluid of a human subject;
    (b) administering the composition of claim 1 to said human subject; and
    (c) continuing said steps of administering and measuring in an amount and for a period of time sufficient to drop the concentration of homocysteine to a low or moderate level of about 4 to 20 µmol/liter in the body fluid.

21. The method of claim 20, wherein the composition administered in step (b) further comprises a therapeutically effective amount of adenosyl methionine or the stable salts thereof.

22. The method of claim 21, wherein the composition administered further comprises a therapeutically effective amount of a vitamin or a pro-vitamin.

23. The method of claim 22, wherein the composition administered further comprises a therapeutically effective amount of an amino acid.

24. The method of claim 20 further comprising the step of measuring additional disease biochemical markers.

25. The method of claim 20 wherein said additional biochemical markers are C-reactive protein (CRP), transthyretin and prostate specific antigen (PSA).

26. The method of claim 20 wherein the step thioretinamide is administered in an amount in the range of about 7.5 mg/70 kg of body weight to 300 mg/70 kg of body weight per day and the pancreatin is administered in an amount in the range about 1.4 g/70 kg of body weight to 14 g/70 kg of body weight per day.

* * * * *